(12) United States Patent
Röhrig

(10) Patent No.: US 7,789,894 B2
(45) Date of Patent: Sep. 7, 2010

(54) PACIFIER FOR A PREMATURE INFANT

(75) Inventor: Peter Röhrig, Vienna (AT)

(73) Assignee: Bamed AG, Altenford (CH)

( * ) Notice: Subject to any disclaimer, the term of this patent is extended or adjusted under 35 U.S.C. 154(b) by 553 days.

(21) Appl. No.: 10/168,920

(22) PCT Filed: Dec. 5, 2000

(86) PCT No.: PCT/AT00/00328

§ 371 (c)(1),
(2), (4) Date: Jun. 24, 2002

(87) PCT Pub. No.: WO01/47467

PCT Pub. Date: Jul. 5, 2001

(65) Prior Publication Data

US 2004/0059381 A1  Mar. 25, 2004

(30) Foreign Application Priority Data

Dec. 23, 1999  (AT)  ................................. A 2179/99

(51) Int. Cl.
*A61J 17/00* (2006.01)
(52) U.S. Cl. ........................................ 606/234
(58) Field of Classification Search ........ D24/194–199; 606/234, 235, 236; 374/151; 128/207.14, 128/207.17; 604/77–79; 446/73
See application file for complete search history.

(56) References Cited

U.S. PATENT DOCUMENTS

| | | | | |
|---|---|---|---|---|
| 3,662,756 A * | 5/1972 | Hakim | ...................... | 606/236 |
| 3,818,906 A * | 6/1974 | Stubbs | ...................... | 606/234 |
| 4,193,407 A * | 3/1980 | Edmark | ...................... | 606/234 |
| 4,715,379 A | 12/1987 | McCormick | | |
| 4,796,628 A | 1/1989 | Anderson | | |
| 4,817,636 A * | 4/1989 | Woods | ...................... | 128/848 |
| 4,909,253 A | 3/1990 | Cook et al. | | |
| 5,052,410 A * | 10/1991 | Stubbs | ...................... | 128/859 |
| 5,078,733 A | 1/1992 | Eveleigh et al. | | |
| 5,176,705 A * | 1/1993 | Noble | ...................... | 604/77 |
| D338,732 S * | 8/1993 | Maradey-Collazo | ....... | D24/194 |
| 5,275,619 A | 1/1994 | Engebretson et al. | | |
| 5,403,349 A * | 4/1995 | Rohrig | ...................... | 606/234 |
| 5,546,938 A | 8/1996 | McKenzie | | |
| 5,642,738 A * | 7/1997 | Lilly, Jr. | ...................... | 128/848 |
| 5,653,731 A * | 8/1997 | Rohrig | ...................... | 606/234 |
| 5,743,648 A * | 4/1998 | Zeindler | ...................... | 374/151 |
| 5,759,195 A * | 6/1998 | Fields et al. | ................ | 606/236 |
| 5,873,892 A * | 2/1999 | Cohen | ...................... | 606/234 |
| 5,954,749 A * | 9/1999 | Fields et al. | ................ | 606/234 |
| 6,080,186 A * | 6/2000 | Pedersen et al. | ........... | 606/234 |
| 6,299,501 B1 * | 10/2001 | Lynch | ...................... | 446/73 |
| 6,447,536 B1 * | 9/2002 | Hinshaw | ...................... | 606/235 |
| 6,514,275 B2 * | 2/2003 | Rohrig | ...................... | 606/234 |
| 6,905,507 B2 * | 6/2005 | Hinshaw | ...................... | 606/235 |

FOREIGN PATENT DOCUMENTS

| | | |
|---|---|---|
| DE | 3728668 | 10/1988 |
| EP | 0847744 | 6/1998 |
| GB | 2278549 A * | 12/1994 |
| WO | 9211836 | 7/1992 |

* cited by examiner

*Primary Examiner*—Darwin P Erezo
(74) *Attorney, Agent, or Firm*—Ladas & Parry LLP

(57) ABSTRACT

A pacifier (1) for premature babies, comprising a shield (2, 2a) on which a nipple (3) as well as, preferably, a grip (4) is provided, and which has at least one recess for the nose, wherein the shield (2, 2a) includes severable portions (6, 6a, 6b) which can be severed at pre-determined severing sites (5, 5a, 5b, 5c) defined as weakened sites or markings.

18 Claims, 4 Drawing Sheets

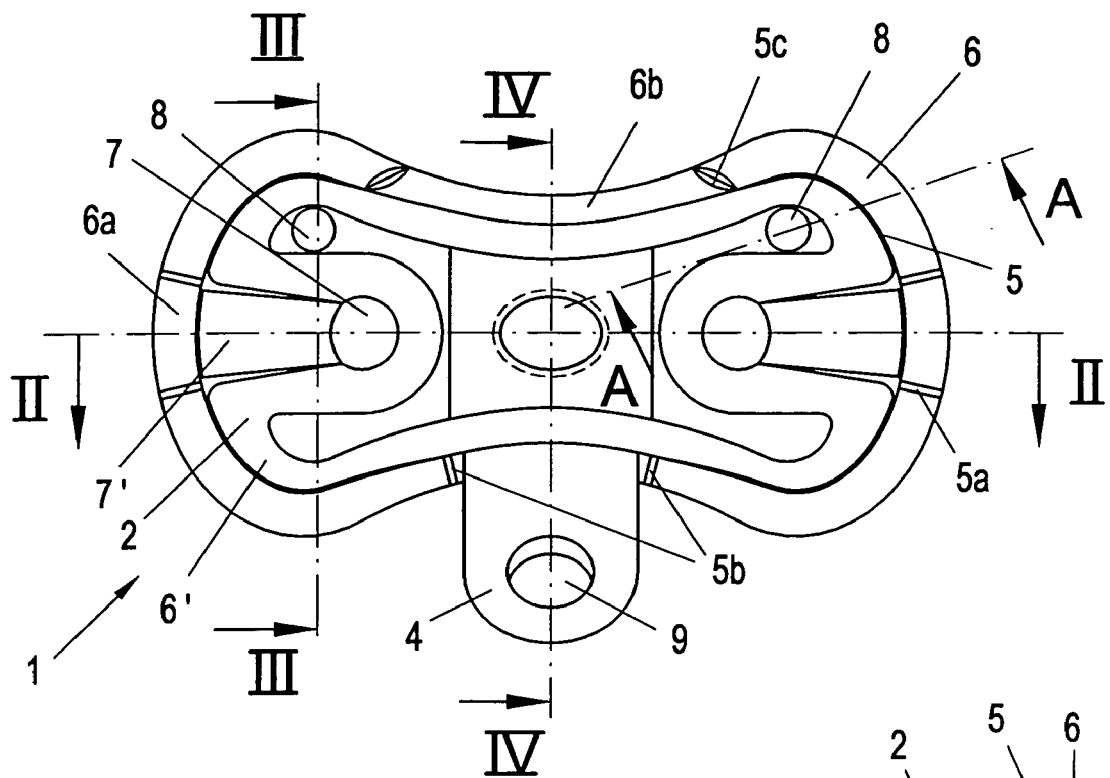
FIG. 1
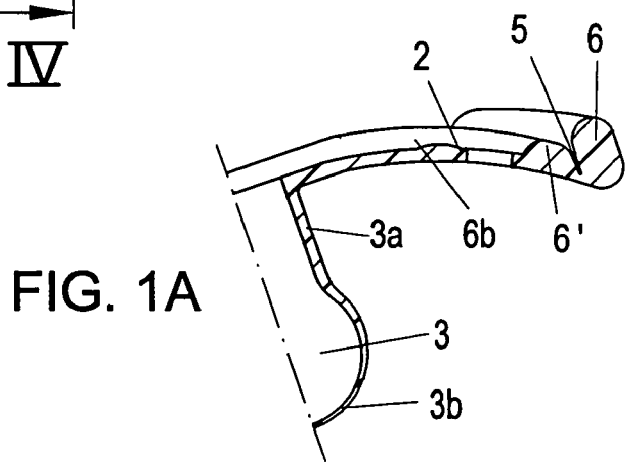
FIG. 1A
FIG. 2
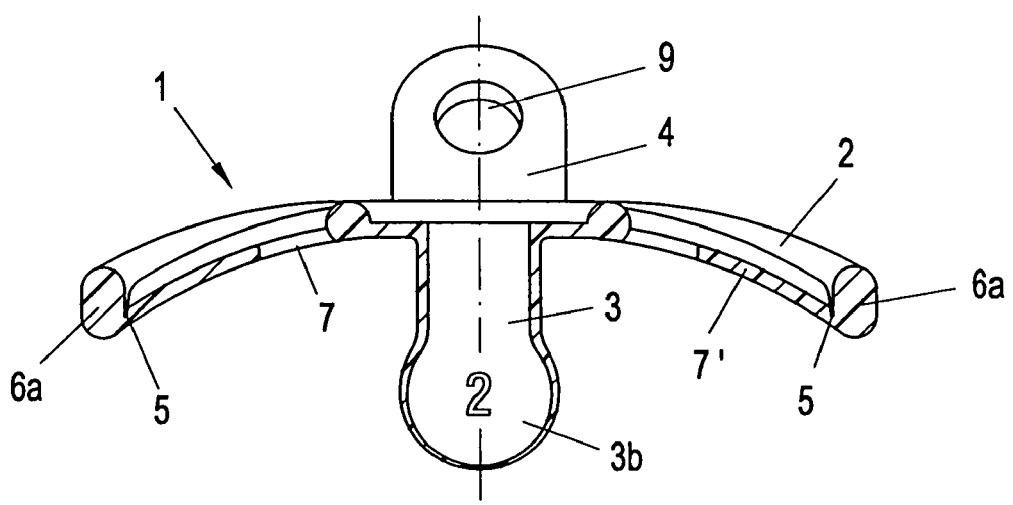

PACIFIER FOR A PREMATURE INFANT

BACKGROUND OF THE INVENTION

1. Field of the Invention

The invention relates to a pacifier for premature babies, comprising a shield on which a nipple as well as, preferably, a grip is provided, and which has at least one recess for the nose.

2. Description of Related Art

In medical tests it has been shown that the use of a pacifier helps premature babies to learn how to drink, whereby they catch up in terms of weight more rapidly. The use of a pacifier does, however, often pose a problem for premature babies since commercially available pacifiers are too big to be used by premature babies. Moreover, premature babies are too small for bottle feeding so that food and also medicaments must be supplied via nasal or mouth intubations, creating problems of space for putting a pacifier into the mouth. A further problem is that the tubes are pressed against the baby's mouth or nose by the pacifier, thereby possibly causing pain.

In U.S. Pat. No. 5,078,733 A a pacifier is described which comprises a shield with a recess for the nose and, optionally, for nasal intubations. This allows for an insertion of the pacifier in the mouth of a premature baby, without having to displace or remove a nasal intubation. However, the mouth intubation is pressed against the premature baby's mouth by the shield, which is detrimental for the premature baby, in particular if this mouth intubation presses against the mouth for an extended period of time.

From WO 92/11836, a pacifier for premature babies is known in which the rim of the shield of the pacifier has an indentation for the nose. The pacifier has smaller dimensions than conventional pacifiers, whereby the pacifier nipple is also prevented from being pushed out of the baby's mouth if the shield knocks against a support when the baby's head is in the lateral lying position. However, also here the insertion of mouth intubations poses a problem.

U.S. Pat. No. 4,796,628 A and DE 37 28 668 A1 relate to pacifiers in which the pacifier shield has lateral recesses for accommodating ducts, or tubes, respectively. Yet here the shield presses against the nose, and furthermore, it is disadvantageous that a uniform size is given so that the pacifier may be to big or too small for the baby, as the case may be.

BRIEF SUMMARY OF THE INVENTION

It is now an object of the invention to provide a pacifier of the initially defined type which is suitable for premature babies of different sizes, an individual adaptation to the respective child being possible and nasal and mouth intubations, respectively, being enabled without any problems.

The inventive pacifier of the initially defined type is characterized in that the shield includes severable portions having associated pre-determined severing sites defined as weakened sites or markings. Due to the portions which are severable from the residual shield, e.g. by tearing, breaking or cutting, the pacifier can be "trimmed" to the respective required size. The pacifier shields become smaller and more handy by severing portions therefrom. Depending on the situation, the severable portions may all be severed, or only the respective inconvenient shield portions are removed. In particular, pacifiers are provided which can be adapted individually when food, air, medicaments etc. are supplied through tubes leading into the baby's nose or mouth, and which also offer sufficient space for intubations. This, on the other hand, allows for the problem-free use of pacifiers in premature babies quite generally, which in turn offers advantages because sucking on a pacifier is advantageous particularly for underdeveloped premature babies since they develop stronger mouth muscles by sucking and also learn drinking more easily; thereby, in turn, they gain weight more rapidly. The pacifier shields have, e.g., approximate dimensions of 20-40 mm×40-60 mm, and in addition to the pre-determined severing sites, further holes may be provided which will ensure drying of the area around the mouth and breathing of the skin, or an emergency breathing of the child if the pacifier is swallowed. On the other hand, production of the pacifier is simplified because merely one uniform size need be produced as regards the shield size.

Within the scope of the present invention, by "weakened sites", areas in the pacifier shield are to be understood which are less resistant to tearing, e.g. because they have a slighter thickness or because of perforations, as compared to the residual pacifier shield. Markings at the severing sites will be particularly advantageous if the desired size of the shield is previously optically determined and also if the severable portions can be cut off by scissors or by a knife, since then an exact cutting at the desired severing sites will be facilitated. The markings may be in the form of dots, lines, hatchings etc. of a color different than the residual pacifier shield.

It is advantageous if a rim region of the shield which, when in use, is located in the nose region, is provided to be severable. If this upper rim region of the shield is severed, space will thereby be provided for nasal intubations so that the tubes can be inserted into the nose or removed therefrom without any problems, without having to remove the pacifier from the child's mouth, so that these manipulations can also be carried out on a sleeping child. Particularly in case of nasal intubations, pacifiers are very important because during a nasal intubation breathing through the mouth will automatically occur, which is not optimal for the development of the baby. By sucking on the pacifier, the baby will switch over to breathing through the nose again, which in turn allows for an optimal development of the premature baby.

Preferably, a rim region of the shield which, when in use, is laterally located in the region of the corners of the mouth, is provided to be severable. By severing this lateral rim portion, space, e.g. in the form of slots, is created for mouth intubations. The pacifier is freely detachable from the tubes, so that the pacifier can be inserted in the mouth and removed therefrom again without having to interrupt the supply of, e.g., food through the tubes. Moreover, also mouth intubations can be inserted in the child's mouth without disturbing the child by removing the pacifier.

Advantageously, the severable rim region which, when in use, is laterally located, is provided as far as to an intubation hole. The intubation hole may be designed such that it has the dimensions of conventially used tubes, ensuring a perfect fit of the tube in the pacifier shield. In this manner, the tubes are maintained in the desired position so as to be put into the premature baby's mouth as centrally as possible and so as not to cause any deformations in the mouth region. By a suitably shaped intubation hole, slipping of the mouth intubation will be largely prevented even if the premature baby's head is moved.

Moreover, it is advantageous if the entire rim of the shield is provided to be severable. This is particularly important if the premature baby is very small and the conventional sizes of pacifier shields are too big. Of course, also several severing sites may be predetermined so that in one and the same pacifier different shield sizes may be provided. As required, the pacifier shield will be trimmed to fit the size of the respective premature baby. Particularly for very small premature babies, a narrow shield is advantageous so that the pacifier will not be pressed out of the premature baby's mouth if the baby rests in a lateral position.

Preferably, the weakened sites are made as tearable material connections. This is, e.g., ensured by shaping or punching holes in the pacifier shield or by areas of locally thinner material so that the shield can be separated along these weakened lines. In this manner, the respective required size of the pacifier shield can be provided rapidly and without additional auxiliary devices.

It is particularly advantageous if the pacifier is made in one piece. This ensures a particularly simple, rapid and low-cost production. In particular for smaller nipple sizes, a single-piece pacifier is particularly suitable.

Preferably, the pacifier is made of silicone, latex, rubber, an elastomer, a thermoplastic material, a thermoplastic elastomer and/or a two-component material, such as, e.g., a thermoplastic material and an elastomer. Also combinations of two or more materials are conceivable. Of course, the requirements on the material as regards its suitability for an infant etc. must be taken into consideration.

It is particularly suitable if the nipple has a single-symmetrical shape. A single-symmetrical shape may, e.g., be provided by inclinedly positioning the nipple relative to the pacifier shield. Thereby it is ensured that the pacifier will be inserted into the child's mouth in the right direction, such as with the indentation for the nose directed upwards, wherein a later turning of the pacifier within the mouth which as such occurs frequently with babies is relatively well prevented by an oblique positioning of the nipple. By the pre-determined orientation of the pacifier within the mouth of the premature baby, twisting of the tubes inserted in recesses and intubation holes of the shield will not occur, either. In addition, due to the single-symmetrical shape, particularly to the oblique positioning of the nipple relative to the pacifier shield, the baby's tongue can be trained so that the premature baby will learn sucking and drinking even more quickly. The nipple shape may furthermore, have various structural elements so as to strengthen the premature baby's tongue and jaw muscles so as to maximally promote the premature baby's development. Furthermore, malpositions of the teeth can be counteracted by nipple shapes suitable in terms of orthodontics.

Preferably, the nipple has a length of from 20 to 30 mm, in particular approximately 20.5 mm or approximately 23 mm, and a maximal width of from 10 to 20 mm, in particular approximately 12.5 mm or approximately 14.5 mm. Smaller nipples can be provided, which have, e.g., a length of approximately 20 mm and a maximal width of approximately 10 mm, which are particularly suitable for very small premature babies. Also somewhat larger nipples may be provided, e.g. with a length of approximately 30 mm and a maximum width of approximately 20 mm. One possibility is to provide three different nipple sizes to cover all weight classes of premature babies: a small size having a length of 20-21 mm and a maximum width of 12-13 mm for babies with a birth weight of up to 1200 g, a middle size having a length of 22-23 mm and a maximum width of 14-15 mm for babies having a weight of 1200 to 1800 g, and a large size having a length of 24-25 mm and a maximum width of 16-17 mm for babies having a weight of 1800 g and more. The pacifier with the large-size nipple is suitable for changing to "normal", commercially available pacifiers.

It is advantageous if the nipple is differently marked according to size. In this manner, the desired nipple can be chosen quickly without having to measure the nipple. The marking may, e.g., be a symbol or number worked into the nipple, printed on the nipple, or punched into the nipple.

For a particularly clear and unambiguous characterization of the nipples it is suitable if the nipple is colored. In this manner, the marking on the nipple need not be looked for, but it can immediately be seen at first sight. In this connection, it is advantageous to choose different, completely distinct colors, such as yellow, green, red, white etc.

Preferably, the nipple is made of silicone. This material has proven particularly suitable for nipples, it is easy to process, and it has a relatively long life.

Particularly preferably the grip has a hole. Through this hole, a string may, e.g., be threaded which will serve to fasten the pacifier to tubes, apparatus, or to the baby's bed. The grip should be shaped such that sufficient space will remain for mouth and nasal intubations: it may be disc-, bow- or bar-shaped.

Preferably, the grip projects obliquely from the shield. For instance, the grip points in the direction away from the recess for the nose, so that the grip will not constitute a spatial impediment for nasal intubations and will not press against the nose, either.

In the following, the invention will be further explained by way of preferred exemplary embodiments illustrated in the drawings. Therein,

BRIEF DESCRIPTION OF THE DRAWINGS FIGURES

FIG. 1 shows a top view onto a pacifier according to the invention;

FIG. 1a shows a partially sectioned view of the pacifier according to line A-A;

FIG. 2 shows a sectional view of the pacifier according to line II-II of FIG. 1;

DETAILED DESCRIPTION OF THE PREFERRED EMBODIMENTS

Figure 3:
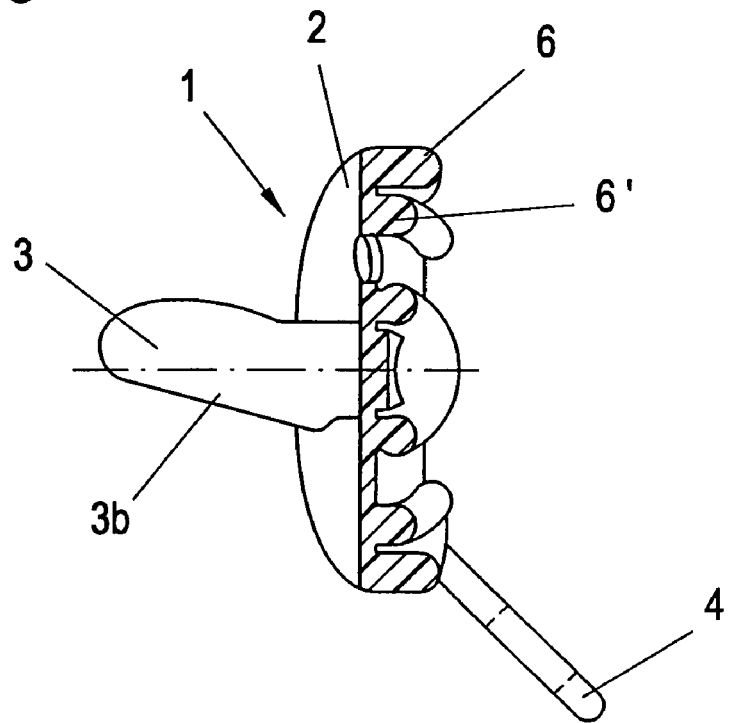
FIG. 3 shows a sectional view of the pacifier according to line III-III of FIG. 1.

In the drawing, a pacifier 1, in which a shield 2 is integrally formed with a nipple 3 and a grip 4 laterally obliquely projecting from the shield 2 at the rim side thereof. The shield 2 comprises separable portions 6, 6a, 6b, associated severing sites 5, 5a, 5b and 5c being designed as locally thinned material areas (or including perforations). The rim region 6 of the shield 2 can be severed as a whole, yet it is also possible that merely, e.g., a part 6a of the rim region 6 located in the lateral region of the corners of the mouth can be severed, a slot 7" being uncovered by removing a web 7' so as to provide access to an intubation hole 7, cf. FIG. 5 in addition to FIGS. 1 and 2. In this manner, an intubation tube (not illustrated in the drawing) can be inserted in the intubation hole 7 through the uncovered slot 7".

By the grip 4 obliquely projecting from the shield at one rim side thereof, the grip 4 will be no spatial impediment for nasal intubations which occur at the oppositely arranged rim side, and the grip 4 will not press against the nose of the respective child, either.

Figure 5:
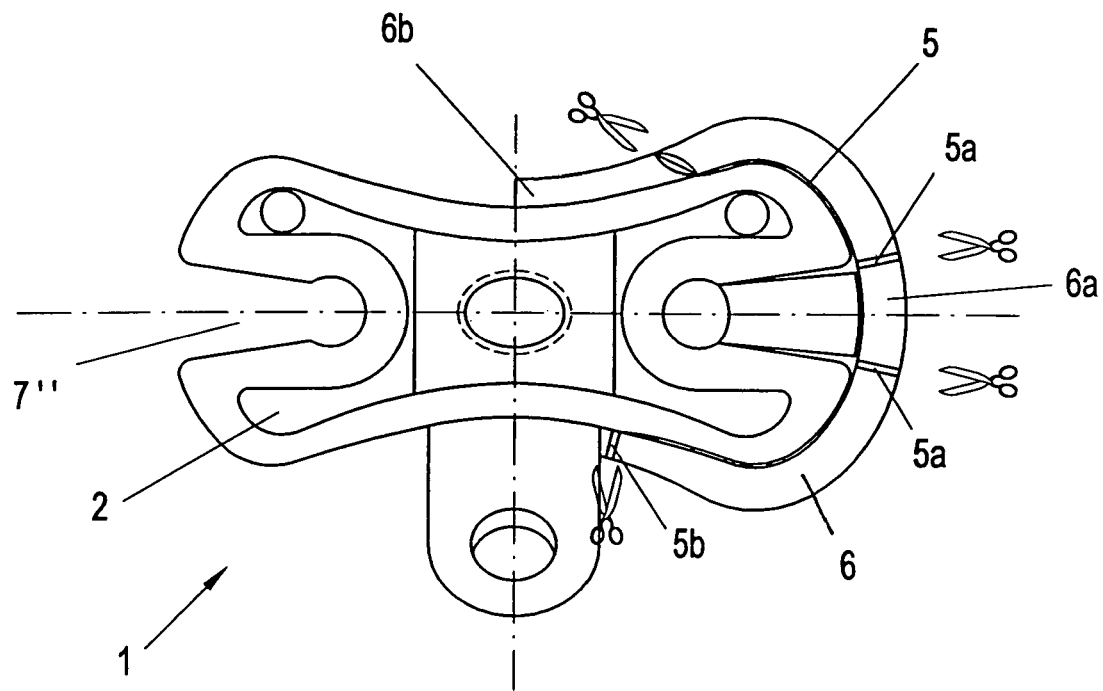
FIG. 5 shows a top view onto the pacifier according to FIG. 1, with part of the separable portions severed.

If the entire rim region 6 is removed by severing at the severing sites 5, a pacifier 1 having a particularly small shield 2 will be obtained, cf. FIG. 5, left-hand side, so as to allow it to be used for premature babies who are very small. If the severing sites 5a in the lateral regions 6a of the corners of the mouth are torn, the slots 7" are uncovered so as to allow for an access to the intubation holes 7. These intubation holes 7 are circular so that in each case an appropriate tube of round cross-section can be positioned therein such that slipping will be prevented. By severing the concave, bow-shaped rim region 6b, the region around the nose is largely freed which is particularly suitable for nasal intubations.

Moreover, breathing holes 8 are provided in the shield 2 which—in case the pacifier 1 is swallowed by the baby and gets stuck in the baby's buccal cavity or pharyngeal region—ensure for an additional possible access of air, i.e. form emergency openings for breathing and thus will prevent suffocation of the baby.

Grip 4 has a hole 9 through which a string or the like can be threaded which will serve to fasten the pacifier 1 to tools, hoses, or to the baby's bed.

In FIG. 1a, the severing site 5 can clearly be seen, it also being visible that the rim region 6 in the region of the corners of the mouth is thicker than a more inwardly located, non-severable rim region 6' (and also thicker than the outward, concave rim region 6b in the nose region).

The nipple 3 comprises a shaft portion 3a and a head portion 3b.

In FIG. 2, the pacifier 1 of FIG. 1 is shown in a sectional representation, it being visible that shield 3 is made with a curvature so that it will optimally contact the baby's mouth area. Grip 4 with hole 9 projects obliquely from a longitudinal side of the shield. Nipple 3 is, e.g., marked with a number "2", which serves to indicate the size of the nipple 3. Instead of this number, the entire nipple 3 or a part thereof, e.g. the head portion 3b, could be specifically colored. In this manner it will be ensured that a pacifier having the correct nipple size will quickly be found for the newborn baby. Furthermore, the intubation holes 7, the thicker rim region 6a for the corners of the mouth and the severing site 5 are visible.

Figure 4:
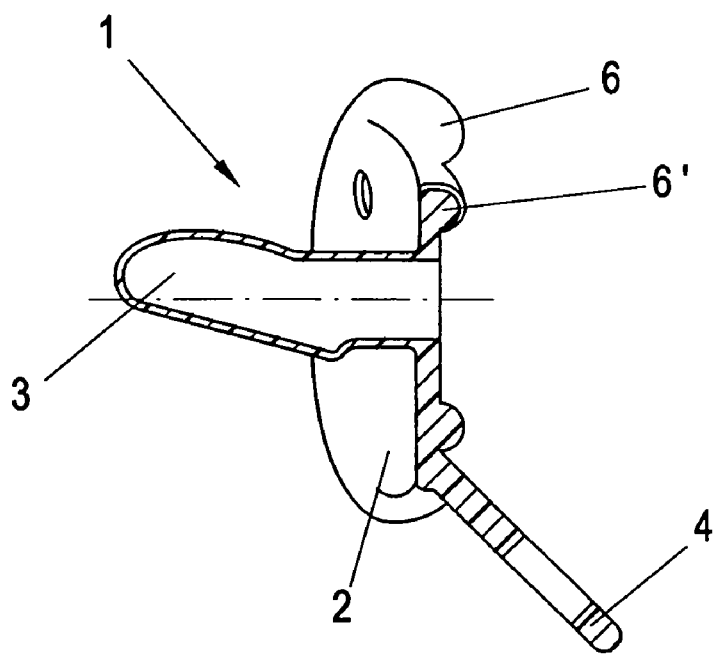
FIG. 4 shows a sectional view of the pacifier according to line IV-IV of FIG. 1.

In FIGS. 3 and 4 it can also be seen that the rim region 6 for the region of the corners of the mouth is thicker than the non-severable rim region 6' located inwardly thereof. From these FIGS. 3 and 4 it can, moreover, be seen in combination with FIGS. 1 and 2 that the nipple 3 or nipple head 3b, respectively, has a single-symmetrical shape, the nipple head 3b being flat on one side and rounded on the other side.

FIG. 4 shows a section according to line IV-IV of FIG. 1, with the concave region 6b of shield 2 having been severed. The inner rim region 6' is visible (in section), and also the non-severed, thicker, severable rim region 6 located therebehind is shown.

FIG. 5 shows a top view of the present pacifier 1, with the severable portions 6, 6a, 6b already having been severed in its left-hand half, whereas these portions are still present on shield 2 in the right-hand half thereof. On the left side, the uncovered slot 7" is shown. The severing site 5 is illustrated by an emphasized line, and scissors-symbols at severing sites 5a, 5b as well as 5c (for the severable region 6b) indicate that at these sites severing by means of scissors, a knife etc. is possible.

Figure 6:
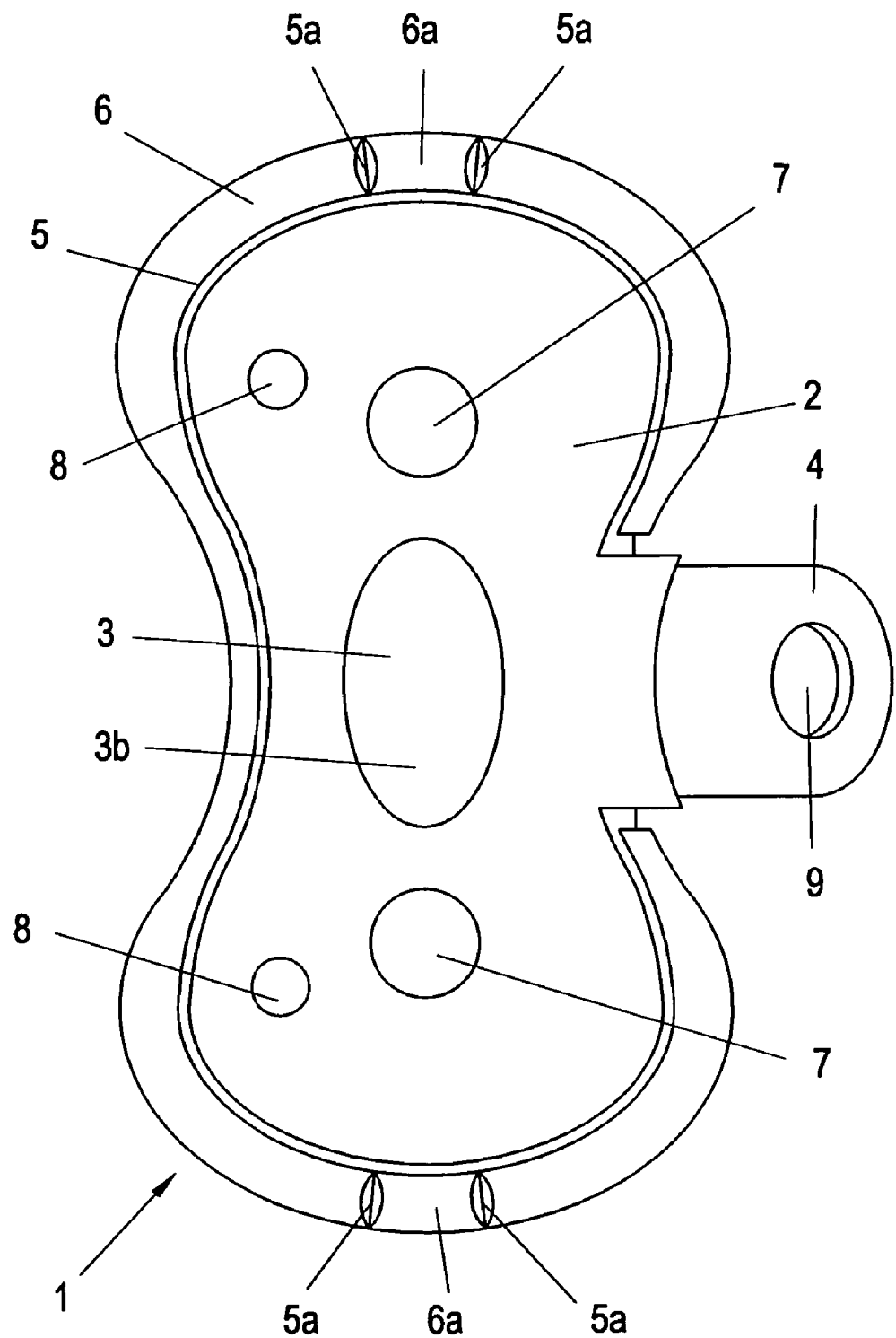
FIG. 6 shows a bottom view of the pacifier according to FIG. 1.

In FIG. 6, the nipple side of pacifier 1 is illustrated, and also at this side of shield 2, the severing sites 5 can be recognized over the entire rim region 6 as well as the severing sites 5a in the lateral regions 6a for the corners of the mouth. Besides, it can be seen that the nipple side of shield 2—which will contact the mouth region of the premature baby when the pacifier 1 is used—is designed to be smooth, except for the intubation holes 7 and the breathing holes 8.

The invention claimed is:

1. A pacifier for premature babies, comprising a shield having a front face where a nipple is provided and which, in use, is turned toward a baby's face, and a rear face opposite the front face, at least one recess for accommodating a baby's nose, an outer rim region and an inner shield body having an inner rim region which is partly adjacent to said outer rim region, said outer rim region as well as said inner rim region of said inner shield body are of major material thickness compared to the material thickness of the rest of the shield, to form thickened outer and inner rim regions, at least one pre-determined severing site provided between said thickened outer rim region and said thickened inner rim region, wherein said predetermined severing site is formed as a notched, weakened line and having reduced material thickness between the front face and the rear face of the shield, said notched weakened line extending in a direction perpendicular to the direction of the material thickness between the front face and the rear face, the pre-determined severing site being located between said inner shield body and said thickened outer rim region and at least partially leading towards an outer edge line of the outer rim region, said thickened outer rim region thus being severable, at least partly, from the inner shield body along said at least one pre-determined severing site so as to adapt the size of the shield to the needs of a premature baby.

2. A pacifier according to claim 1, wherein a grip is provided on said shield.

3. A pacifier according to claim 2, wherein the grip has a hole.

4. A pacifier according to claim 3, wherein the grip obliquely projects from the shield.

5. A pacifier according to claim 1, wherein the outer rim region which, when in use, is located in the nose region of a baby, is provided to be severable.

6. A pacifier according to claim 1, wherein an entire outer rim region of the shield is provided to be severable.

7. A pacifier according to claim 1, wherein the severing sites are made as tearable material connections.

8. A pacifier according to claim 1, wherein the pacifier is made in one piece.

9. A pacifier according to claim 1, wherein the pacifier is made of silicone, latex, rubber, an elastomer, a thermoplastic material, a thermoplastic elastomer and/or a two-component material.

10. A pacifier according to claim 1, wherein the nipple has a single-symmetrical shape.

11. A pacifier according to claim 1, wherein the nipple has a length of from 20 to 30 mm, and a maximum width of from 10 to 20 mm.

12. A pacifier according to claim 1, wherein the nipple has a length of from 20.5 mm to 23 mm, and a maximum width of from 12.5 mm to 14.5 mm.

13. A pacifier according to claim 1, wherein the nipple is differently marked according to size.

14. A pacifier according to claim 13, wherein the nipple is colored.

15. A pacifier according to claim 1, wherein the nipple is made of silicone.

16. A pacifier according to claim 1, wherein the outer rim region which, when in use, is laterally located in the region of the corners of the mouth of a baby, is provided to be severable.

17. A pacifier according to claim 16, wherein the severable outer rim region which, when in use, is laterally located, is provided as far as to an intubation hole.

18. A pacifier according to claim 1, wherein the notched weakened line extends around the circumference of the inner shield body.

* * * * *